(12) United States Patent
Martin et al.

(10) Patent No.: US 10,492,496 B2
(45) Date of Patent: Dec. 3, 2019

(54) DISINFECTANT FORMULATION COMPRISING CALCIUM HYDROXIDE AND SODIUM HYPOCHLORITE

(71) Applicant: Biosenta, Inc., Toronto (CA)

(72) Inventors: Marcus E. Martin, Parry Sound (CA); Edward K. Pardiak, Cote-Saint-Luc (CA)

(73) Assignee: Biosenta, Inc., Toronto (CA)

( * ) Notice: Subject to any disclaimer, the term of this patent is extended or adjusted under 35 U.S.C. 154(b) by 0 days.

(21) Appl. No.: 15/378,552

(22) Filed: Dec. 14, 2016

(65) Prior Publication Data

US 2017/0094977 A1 Apr. 6, 2017

Related U.S. Application Data

(62) Division of application No. 14/426,415, filed as application No. PCT/CA2013/050693 on Sep. 9, 2013.

(60) Provisional application No. 61/698,076, filed on Sep. 7, 2012.

(51) Int. Cl.
*A01N 59/00* (2006.01)
*A01N 59/06* (2006.01)
*A61L 2/18* (2006.01)

(52) U.S. Cl.
CPC ............ *A01N 59/06* (2013.01); *A01N 59/00* (2013.01); *A61L 2/18* (2013.01)

(58) Field of Classification Search
CPC ............ A01N 59/06; A01N 59/00; A61L 2/18
See application file for complete search history.

(56) References Cited

U.S. PATENT DOCUMENTS

| 3,954,948 | A | 5/1976 | Sakowski | |
| 2005/0109981 | A1* | 5/2005 | Tucker | A01N 59/00 252/186.38 |
| 2006/0089285 | A1 | 4/2006 | Ahmed et al. | |
| 2010/0239690 | A1* | 9/2010 | Noda | A61K 9/0014 424/693 |
| 2015/0044144 | A1* | 2/2015 | Lin | A01N 59/00 424/10.3 |

FOREIGN PATENT DOCUMENTS

| CA | 2311485 A1 | 12/2000 |
| KR | 100865979 B1 * | 10/2008 |
| KR | 100865979 B1 | 10/2008 |
| WO | 9006682 A1 | 6/1990 |
| WO | 9428722 A1 | 12/1994 |

OTHER PUBLICATIONS

Bates et al. Calcium Hydroxide as a Highly Alkaline pH Standard. Journal of Research of the National Bureau of Standards, 1956, 56(6):305-312.*
English language abstract for KR 100865979 B1 (2008).
Farhad et al., Evaluation of the antibacterial effect of calcium hydroxide in combination with three different vehicles: An in vitro study, Dent Res J (Isfahan), 2012, 9(2), pp. 167-172.
National Lime Association, Lime Fact Sheet: Properties of typical commercial lime products, 2011, pp. 1-8.
International Search Report for PCT/CA2013/050693 dated Jan. 7, 2014.
Supplementary European Search Report for EP 13 83 5706 dated Mar. 30, 2016.

* cited by examiner

*Primary Examiner* — Frederick F Krass
*Assistant Examiner* — Olga V Tcherkasskaya
(74) *Attorney, Agent, or Firm* — Caesar Rivise, PC

(57) ABSTRACT

This application relates to disinfectant formulations including calcium hydroxide and sodium hypochlorite and further relates to method of manufacturing the disinfectant formulations and methods of using the formulations.

2 Claims, 2 Drawing Sheets

DISINFECTANT FORMULATION COMPRISING CALCIUM HYDROXIDE AND SODIUM HYPOCHLORITE

CROSS REFERENCE TO PRIOR APPLICATIONS

The present application claims priority under the Paris Convention to U.S. Application No. 61/698,076, filed Sep. 7, 2012, the entire contents of which are incorporated herein by reference.

FIELD OF THE INVENTION

The present invention relates to disinfectant formulations and in particular to formulations comprising calcium hydroxide and sodium hypochlorite for disinfecting surfaces.

BACKGROUND OF THE INVENTION

The health effects caused by bacteria, fungus, mold, viruses and other micro-organisms that can grow on surfaces is a serious concern, especially in the food service and preparation industry and in the medical field.

Disinfectants are substances that are applied to non-living objects to destroy microorganisms that are living on the objects. Generally, disinfectants work by destroying the cell wall of microbes or interfering with the metabolism. Various disinfectants have been used with mixed results. Often the most efficacious disinfectants also have harmful side effects to the individuals who use them.

For example, solutions containing sodium hypochlorite are commonly used as disinfectants, however these products can release harmful chlorine vapours which can have negative health consequences such as impaired respiratory health. This is particularly the case where high concentrations of hypochlorite are used. Hypochlorite solutions are often combined with sodium hydroxide which acts to stabilize the hypochlorite and prevent decomposition to chlorine. However, the addition of the substantial amounts of sodium hydroxide required for stabilization, results in solutions that are highly caustic and therefore also harmful for those handling such solutions.

There is a need for disinfecting agents that are effective in disinfecting surfaces but that are less harmful to those who have to use them.

SUMMARY OF THE INVENTION

The present invention relates to a disinfectant formulation comprising calcium hydroxide ($Ca(OH)_2$) and sodium hypochlorite (NaClO). In one embodiment the disinfectant formulation is an aqueous solution comprising about 0.1% to about 5% v/v sodium hypochlorite (NaClO) and about 0.12% to about 0.18% v/v calcium hydroxide ($Ca(OH)_2$).

In a particular embodiment, the disinfectant formulation is prepared by forming a supernatant solution of calcium hydroxide in water having a concentration of about 0.12% to 0.18% and combining the supernatant with about 0.1% to 5% by volume of sodium hypochlorite.

In a further aspect, there is provided a method of disinfecting objects comprising applying the disinfecting formulation to said object to destroy microorganisms living on said object. Said microorganisms including bacteria, fungus, mold, viruses and/or other microbes.

BRIEF DESCRIPTION OF THE DRAWINGS

The features of the invention will be described in relation to the appended drawings in which.

DETAILED DESCRIPTION OF THE INVENTION

Figure 1:
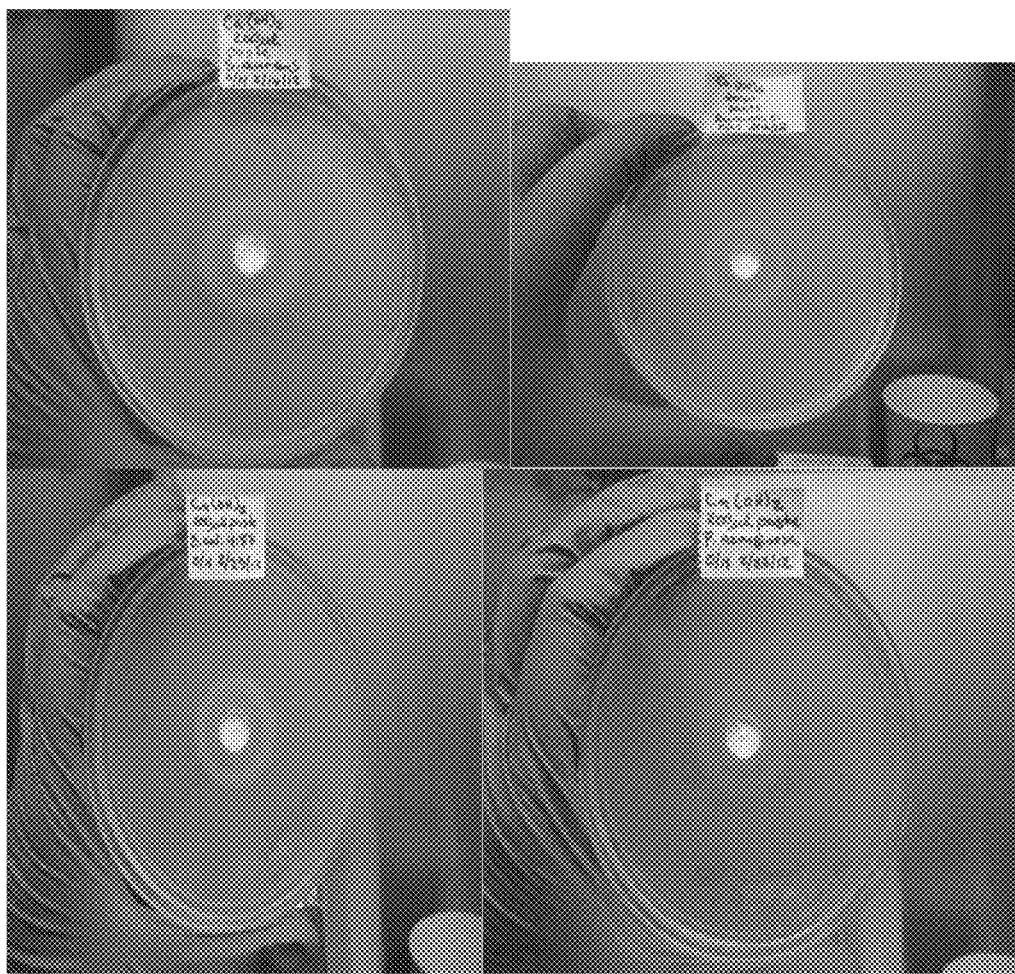
FIG. 1 is a picture showing a typical zone of inhibition of 200 µl of $Ca(OH)_2$ paste against 4 bacteria, overnight A) *S. Aureus,* B) *Salmonella,* C) *E. Coli* and D) *Pseudomonas aeruginosa.*
Figure 2:
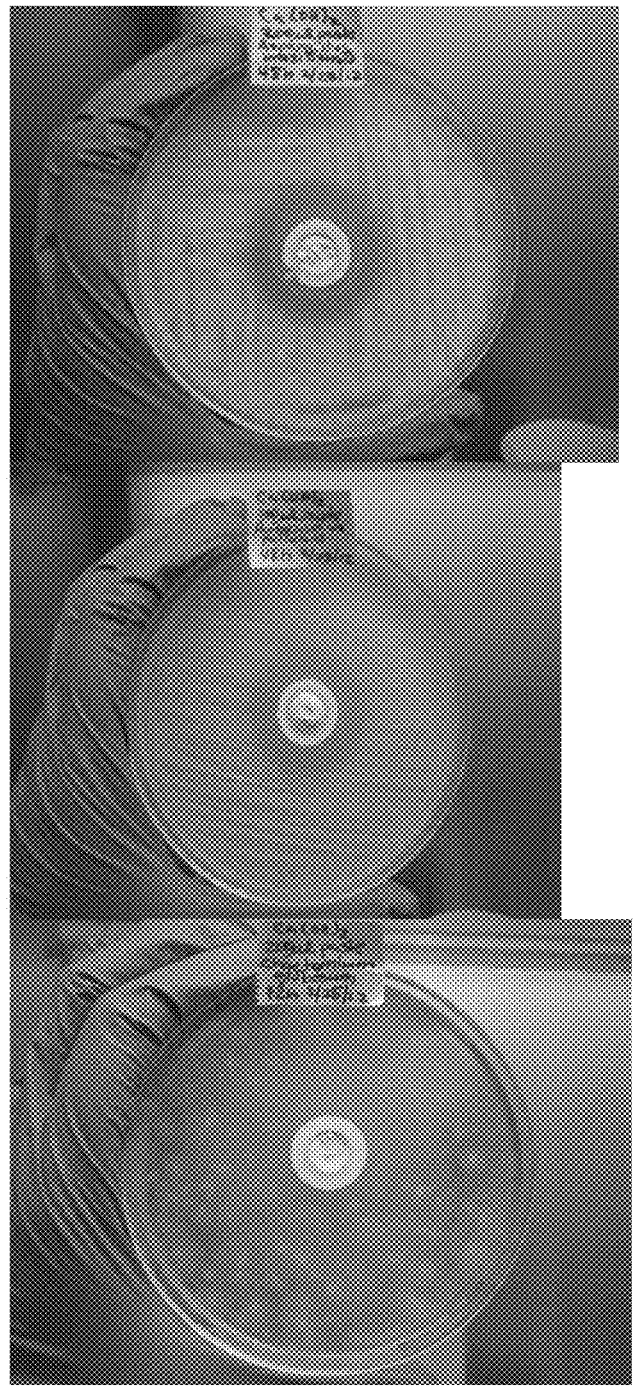
FIG. 2 shows a picture of a typical zone of inhibition of 200 µl of $Ca(OH)_2$ paste against three fungi, A) *Aspergillus niger* (48 hr) B) *Auriobasidum pullulans* (48 hr) and C) *Chaetobium, glabosom* (72 hr).

It has been found that $Ca(OH)_2$ acts to stabilize hypochlorite in solution. By stabilizing the hypochlorite, the release of toxic chlorine gas may be reduced. Further it has been found that less $Ca(OH)_2$ is required to stabilize hypochlorite in solution as compared to the amount of NaOH that would be required to achieve a similar result. Since less $Ca(OH)_2$ can be used, the resulting formulation can be less caustic and therefore less harmful to the user.

It has also been found that the use of $Ca(OH)_2$ results in less precipitation than using NaOH to stabilize hypochlorite. This is particularly advantageous in the application of the disinfectant formulation as a spray disinfectant where the precipitate can cause spray nozzles to become clogged and malfunction.

Ion channels in a cell serve many functions apart from electrical signal transduction: chemical signaling, ($Ca^{2+}$ as a second messenger), transepithelial transport, regulation of cytoplasmic or vesicular ion concentration and pH, and regulation of cell volume. Therefore, ion channel dysfunction can cause cell disruption and in the case of calcium channels, alter pH and cellular osmotic pressure. It is believed that the $Ca(OH)_2$ acts through the calcium channel to disrupt the normal cell function and ultimately kill the cell, providing further antimicrobial action in the formulation.

This mechanism of action of $Ca(OH)_2$ is believed to be different from the action of NaOH which acts on the cell membrane, lipids and proteins, thereby denaturing and weakening cell membrane surface structure and resulting in cell death.

In an embodiment of the invention the disinfectant formulation comprises an aqueous solution with about 0.1% to about 5% v/v sodium hypochlorite (NaClO) and about 0.12% to about 0.18% v/v calcium hydroxide ($Ca(OH)_2$). In a further embodiment the solution comprises about 0.1% to about 3% v/v sodium hypochlorite. In another embodiment the solution comprises about 0.125% to about 2.5% sodium hypochlorite. In still another embodiment the solution comprises 0.125% sodium hypochlorite. In yet another embodiment the solution comprises 2.5% sodium hypochlorite.

In a further aspect there is provided a method of manufacturing a disinfectant solution. In one embodiment the method comprises mixing 97% pure calcium hydroxide ($Ca(OH)_2$) dry powder with deionized water. In a particular embodiment the calcium hydroxide powder is 200 mesh size. In one embodiment the percentage ratio of calcium hydroxide to deionized water is about 2.5 to about 97.5 by weight, to produce a supernatant. The concentration of calcium hydroxide in the supernatant is controlled by temperature to be about 0.12% to about 0.18%. Sodium hypochlorite NaClO) is added to the supernatant. The solution concentration of sodium hypochlorite is in the range of from about 0.01% to about 5% by volume. In a further embodiment sodium hypochlorite is in a rage from about 0.1% to about 3% by volume. In a particular example the sodium hypochlorite concentration is about 0.125% by volume. In another example the sodium hypochlorite concentration is about 2.5% by volume.

It has further been found that incorporating a calcium hydroxide supernatant having a pH of about 12.1-12.6 in the disinfectant solution allows pH stability to be maintained over a longer period of time due to a high pH environment in the solution.

In a further embodiment the disinfectant formulation is prepared in a compounding batch process using large mixing and storage tanks. The decantation of supernatant having solid concentration of about 0.12% to about 0.18% is controlled by temperature. From storage, the solution is pumped to a final mix tank where sodium hypochlorite solution is metered into the bottling lines. In a particular example, 0.125% of sodium hypochlorite is metered into the bottling line.

In a further aspect the disinfectant formulation can be packaged in various types and sizes of containers for example 946 ml, 4 L and 10 L containers.

In still a further aspect, the disinfectant formulation can be used to disinfect non-living objects. In a particular aspect, the formulation can be used to disinfect hard surfaces by applying the formulation to the surface. In certain applications, the formulation may be left on the surface for a specific period of time. For example, the disinfectant formulation may be left on the surface for a period ranging from about 5 minutes to about 24 hours.

In a further aspect the disinfectant formulation may be used to kill microbes on an object to which it is applied. The microbes may be bacteria, fungus, mold, viruses and other micro-organisms. Examples of some micro-organisms which may be killed by the disinfectant formulation include *Herpes Simplex Virus, Staphylococcus aureus, Salmonella enteric, E. Coli, Pseudomonas aeruginosa, Aspergillus niger, Auriobasidium pullulans* and *Chaetobium globosom*. It will be understood by one of skill in the art that the above list of micro-organisms is merely provided to illustrate the invention and that the disinfecting formulation is expected to be active against other micro-organisms.

Experiments

A. Investigating the Antiviral Properties of $Ca(OH)_2$

Experiments: 10 µL of virus stock was mixed with 100% saturated $Ca(OH)_2$ (Final $Ca(OH)_2$ concentration 99%) and incubated for different lengths of time. Then the mixture was diluted and the viable number of virus (Log TCID) was measured.

Results:

99% saturated $Ca(OH)_2$ was used to treat 2 viruses using different incubation times (5 min to 1 hr). The preliminary result for HSV-1 is shown in table 1 below:

TABLE 1

| Log TCID50/ 100 ul | 0 min | 5 min | 10 min | 15 min | 30 min | 60 min |
|---|---|---|---|---|---|---|
| HSV-1 | 6.5 | 6 | 5.5 | 3.5 | 3 | <3 |

Conclusion: $Ca(OH)_2$ saturated solution is effective against *Herpes Simplex Virus*(HSV-1, >3.5 log kill in 1 hr).

B. Investigating the Biocidal Properties of $Ca(OH)_2$

Experiments: After confirmation regarding the observed morphologies of *E. coli* and *Pseudomonas*, tests were conducted to investigate the biocidal properties of $Ca(OH)_2$. An efficacy study against fungi was also completed.

Results:

TABLE 2

Antimicrobial Susceptibility Testing $Ca(OH)_2$ paste (a complete study)

| Bacteria Organism | Paste volume | Zone of Inhibition (mm) | | |
|---|---|---|---|---|
| | | 16-18 hr | 24 hr | 48 hr |
| *Staphylococcus aureus* (# 6538) | 0.2 ml | 19, 19, 18 | 18, 17, 18 | 18, 17-18, 18 |
| | 0.3 ml | 19, 18, 18-19 | 19, 18, 18 | 17, 18, 18 |
| *Salmonella enteric* (# 6994) | 0.2 ml | 21, 21, 21 | 21, 20, 21 | 21, 20-21, 21 |
| | 0.3 ml | 23, 21, 22 | 23, 22, 22 | 22, 21-22, 21 |
| *E. Coli* (#4157) | 0.2 ml | 20, 20, 19 | 20, 17, 18 | 17, 17, 17 |
| | 0.3 ml | 20, 20, 20 | 18, 20, 18 | 18, 19, 18 |
| *E. Coli* (# 12810) | 0.2 ml | 16, 16, 17 | 16, 16, 16 | 16, 16, 16 |
| | 0.3 ml | 17, 17, 17 | 17, 17, 16-17 | 17, 17, 16 |
| *Pseudomonas aeruginosa* (#13388) | 0.2 ml | 17, 17, 17 | 16, 17, 16 | 16, 16, 16 |
| *Pseudomonas aeruginosa* (#13388) | 0.3 ml | 17, 17, 17 | 17, 17, 17 | 17, 16, 17 |

| Fungi Organism | Paste volume | 24 hr | 48 hr | 72 hr |
|---|---|---|---|---|
| *Aspergillus niger*(#9642) | 0.2 ml | —, ~35≠, — | 30, 30, 28-29 | 22, 23, 21 |
| | 0.3 ml | —, ~34≠, — | 29, 30, 27-28 | 22, 23, 21 |
| *Auriobasidum pullulans*(#15233) | 0.2 ml | 27, 29, 29 | 23-24, 24-25, 23-24 | 22, 22, 20 |
| | 0.3 ml | 30, 30, 30 | 25-26, 26-27, 27 | 22, 22, 23 |
| *Chaetobium globosom*(#6295) | 0.2 ml | —, —, — | —, —, — | 23, 22, 22 |
| | 0.3 ml | —, —, — | —, —, — | 25, 24, — |

"—" means patchy (partial) lawn because fungi grows much slower.
"≠" means very spotty growth, not yet a confluence lawn.

Quality negative control: 200 µL of sterile water was added to 8 mm bore hole, all showed no sign of microbial inhibition (0 mm past 8 mm bore).

Antibacterial Activity Test

A germicidal spray test was carried out to test the efficacy of a disinfectant formulation of the invention comprising a concentration of calcium hydroxide of 0.12% to 0.18% in water and 2.5% sodium hypochlorite by volume. The efficacy was tested against *S. aureus*. The test was conducted on 30 sterile 18×36×1 mm glass slides as the carrier. No soil was added. The samples were incubated for 48±6 hours at an incubation temperature of 36.0±1° C. The samples were sprayed with 3 sprays of the disinfectant and left for a contact time of 5 minutes at ambient temperature. The neutralizer was 20 ml Modified Letheen Broth (w/0.1% sodium thoisulfate).

TABLE 3

Germicidal Spray Test Results

| Test Substance | Soil load | Contact time | Microorganism | Average CFU/Carrier | Carriers Positive | Carriers negative |
|---|---|---|---|---|---|---|
| supernatant composition of 0.12-0.18% Ca(OH)$_2$ in water with 2.5% sodium hypochlorite | None | 5 minutes | *S. Aureus* ATCC 6538 | 8.10E+05 | 0 | 30 |

Antiviral Activity Test

An experiment was conducted to investigate the antiviral properties of a disinfecting formulation of the invention. A disinfecting formulation comprising 0.12-0.18% of calcium hydroxide and 0.125% sodium hypochlorite was mixed with 10 µL of virus stock. The sample was at a pH or 12.64 as measured and incubated for different time periods. The mixture was then diluted and the viable number of virus (Log TCID) was measured.

Study Results

| Log TCID50/ 100 µL | 0 min | 5 min | 10 min | 1 hr | 2 hr | 24 hr |
|---|---|---|---|---|---|---|
| HSV-1 virus | 6.6 | <3 | <3 | <3 | <3 | <3 |
| EMCV virus | 7 | 5.3 | 3.5 | 3 | 3 | <3 |

The disinfectant formulation was found to be very effective against *Herpes Simplex Virus* (HSV-1), (>3.5 log kill within 5 min.), and very effective (3.5 log kill within 10 min,) against *Encephalomyocarditis* (EMCV) virus.

What is claimed is:

1. A method of manufacturing a disinfectant formulation comprising calcium hydroxide (Ca(OH)$_2$) and sodium hypochlorite (NaClO), said method comprising:
    a) mixing calcium hydroxide dry powder with water in a percentage ratio of about 2.5 to about 97.5 by weight to form a supernatant of calcium hydroxide in water having a dissolved solids concentration of about 0.12% to about 0.18% by volume of calcium hydroxide in the supernatant; the dissolved solids concentration of calcium hydroxide in the supernatant being controlled by adjusting the temperature;
    b) separating the supernatant from precipitated calcium hydroxide; and
    c) adding to the supernatant separated from the precipitated calcium hydroxide sodium hypochlorite in an amount to achieve a solution concentration of about 0.1% to 5% by volume.

2. The method of claim 1, wherein the calcium hydroxide dry powder is 97% pure and has a size of 200 mesh and wherein the water is deionized.

* * * * *